(12) United States Patent
Sugiyama (10) Patent No.: US 11,369,656 B2
(45) Date of Patent: *Jun. 28, 2022

(54) IMMUNOTHERAPY FOR ANGIOGENIC DISEASE

(71) Applicant: International Institute of Cancer Immunology, Inc., Suita (JP)

(72) Inventor: Haruo Sugiyama, Minoo (JP)

(73) Assignee: International Institute of Cancer Immunology, Inc., Suita (JP)

(*) Notice: Subject to any disclaimer, the term of this patent is extended or adjusted under 35 U.S.C. 154(b) by 195 days.

This patent is subject to a terminal disclaimer.

(21) Appl. No.: 16/592,407

(22) Filed: Oct. 3, 2019

(65) Prior Publication Data

US 2020/0023029 A1    Jan. 23, 2020

Related U.S. Application Data

(62) Division of application No. 15/534,895, filed as application No. PCT/JP2015/084709 on Dec. 10, 2015, now Pat. No. 10,525,096.

(51) Int. Cl.
| | |
|---|---|
| *C07K 7/06* | (2006.01) |
| *A61P 27/02* | (2006.01) |
| *C07K 7/04* | (2006.01) |
| *A61K 38/02* | (2006.01) |
| *A61K 39/00* | (2006.01) |
| *C07K 14/47* | (2006.01) |
| *A61K 35/17* | (2015.01) |
| *A61K 9/00* | (2006.01) |

(52) U.S. Cl.
CPC .............. *A61K 38/02* (2013.01); *A61K 35/17* (2013.01); *A61K 39/00* (2013.01); *A61K 39/0011* (2013.01); *A61K 39/001153* (2018.08); *A61P 27/02* (2018.01); *C07K 7/04* (2013.01); *C07K 7/06* (2013.01); *C07K 14/4748* (2013.01); *A61K 9/006* (2013.01); *A61K 9/0019* (2013.01)

(58) Field of Classification Search
None
See application file for complete search history.

(56) References Cited

U.S. PATENT DOCUMENTS

| | | |
|---|---|---|
| 7,063,854 B1 | 6/2006 | Gaiger et al. |
| 7,312,243 B1 | 12/2007 | Pravda |
| 2008/0070835 A1 | 3/2008 | Sugiyama |
| 2010/0292160 A1 | 11/2010 | Sugiyama |
| 2011/0070251 A1 | 3/2011 | Sugiyama |
| 2011/0098233 A1 | 4/2011 | Sugiyama |
| 2012/0045465 A1 | 2/2012 | Sugiyama |
| 2014/0220057 A1 | 8/2014 | Okubo et al. |
| 2014/0220059 A1 | 8/2014 | Asari et al. |
| 2015/0328278 A1 | 11/2015 | Kubo et al. |
| 2018/0170986 A1 | 6/2018 | Sugiyama |

FOREIGN PATENT DOCUMENTS

| | | |
|---|---|---|
| JP | 2014-169276 A | 9/2014 |
| JP | 2014-169282 A | 9/2014 |
| WO | 2002-525099 A | 8/2002 |
| WO | 2005/045027 A1 | 5/2005 |
| WO | 2007/097358 A1 | 8/2007 |
| WO | 2008/081701 A1 | 7/2008 |
| WO | 2009/072610 A1 | 6/2009 |
| WO | 2010/123065 A1 | 10/2010 |
| WO | 2014/098012 A1 | 6/2014 |

OTHER PUBLICATIONS

Office Action dated Mar. 23, 2021 in co-pending U.S. Appl. No. 16/692,598, 16 pages.
Kim L Morrison, et al., "Combinatorial alanine-scanning," Current Opinion in Chemical Biology, vol. 5, 2001, pp. 302-307.
Wagner, et al., "The Wilms' tumour suppressor WT1 is involved in endothelial cell proliferation and migration: expression in tumour vessels in vivo," Oncogene, 2008, vol. 27, No. 26, pp. 3662-3672.
International Search Report dated Mar. 1, 2016 in PCT/JP2015/084709 filed Dec. 10, 2015.
Sporn, "Chemoprevention of Cancer", Carcinogenesis, vol. 21 (2000), pp. 525-530.
Extended European Search Report dated May 18, 2018 in Patent Application No. 15867628.8, 7 pages.
Amin, et al. "WT1 Mutants Reveal SRPK1 to Be a Downstream Angiogenesis Target by Altering VEGF Splicing", Cancer Cell, vol. 20, No. 6, XP002780581, Dec. 13, 2011, pp. 768-780.
Koido, et al. "Treatment with Chemotherapy and Dendritic Cells Pulsed with Multiple Wilms' Tumor (WT1)—Specific MHC Class I/II—Restricted Epitopes for Pancreatic Cancer", Clinical Cancer Research, vol. 20, No. 16, XP002780582, Aug. 15, 2014, pp. 4228-4239 (with cover page).
International Preliminary Report on Patentability and Written Opinion dated Jun. 22, 2017 in PCT/JP2015/084709 (with English language translation).
Office Action dated Aug. 22, 2017, in corresponding Japanese Patent Application No. 2016-563738 (with English-abridged translation).
Watanabe et al., "Transcription Factor Ets-1 Mediates Ischemia- and Vascular Endothelial Growth Factor-Dependent Retinal Neovascularization," American Journal of Pathology, (2004) vol. 164, No. 5, pp. 1827-1835.
Non-Final Office Action dated Jul. 3, 2019, issued in U.S. Appl. No. 15/831,484.
U.S. Office Action dated Nov. 30, 2021 in U.S. Appl. No. 16/692,598.

*Primary Examiner* — Thomas S Heard
(74) *Attorney, Agent, or Firm* — Oblon, McClelland, Maier & Neustadt, L.L.P.

(57) ABSTRACT

The present invention provides a pharmaceutical composition containing a cancer antigen peptide for treatment and prevention of angiogenic diseases.

6 Claims, 5 Drawing Sheets

Specification includes a Sequence Listing.

SEQUENCE LISTING

<160> NUMBER OF SEQ ID NOS: 40

<210> SEQ ID NO 1
<211> LENGTH: 9
<212> TYPE: PRT
<213> ORGANISM: Homo sapiens

<400> SEQUENCE: 1

Arg Met Phe Pro Asn Ala Pro Tyr Leu
1               5

<210> SEQ ID NO 2
<211> LENGTH: 9
<212> TYPE: PRT
<213> ORGANISM: Homo sapiens

<400> SEQUENCE: 2

Arg Tyr Pro Ser Cys Gln Lys Lys Phe
1               5

```
<210> SEQ ID NO 3
<211> LENGTH: 9
<212> TYPE: PRT
<213> ORGANISM: Homo sapiens

<400> SEQUENCE: 3

Arg Tyr Phe Pro Asn Ala Pro Tyr Leu
1               5

<210> SEQ ID NO 4
<211> LENGTH: 9
<212> TYPE: PRT
<213> ORGANISM: Homo sapiens

<400> SEQUENCE: 4

Ala Tyr Leu Pro Ala Val Pro Ser Leu
1               5

<210> SEQ ID NO 5
<211> LENGTH: 9
<212> TYPE: PRT
<213> ORGANISM: Homo sapiens

<400> SEQUENCE: 5

Asn Tyr Met Asn Leu Gly Ala Thr Leu
1               5

<210> SEQ ID NO 6
<211> LENGTH: 9
<212> TYPE: PRT
<213> ORGANISM: Homo sapiens

<400> SEQUENCE: 6

Asp Gln Leu Lys Arg His Gln Arg Arg
1               5

<210> SEQ ID NO 7
<211> LENGTH: 9
<212> TYPE: PRT
<213> ORGANISM: Homo sapiens

<400> SEQUENCE: 7

Val Thr Phe Asp Gly Thr Pro Ser Tyr
1               5

<210> SEQ ID NO 8
<211> LENGTH: 9
<212> TYPE: PRT
<213> ORGANISM: Homo sapiens

<400> SEQUENCE: 8

Gln Gly Ser Leu Gly Glu Gln Gln Tyr
1               5

<210> SEQ ID NO 9
<211> LENGTH: 9
<212> TYPE: PRT
<213> ORGANISM: Homo sapiens

<400> SEQUENCE: 9

Cys Met Thr Trp Asn Gln Met Asn Leu
1               5
```

-continued

```
<210> SEQ ID NO 10
<211> LENGTH: 9
<212> TYPE: PRT
<213> ORGANISM: Homo sapiens

<400> SEQUENCE: 10

Leu Ser His Leu Gln Met His Ser Arg
1               5

<210> SEQ ID NO 11
<211> LENGTH: 9
<212> TYPE: PRT
<213> ORGANISM: Homo sapiens

<400> SEQUENCE: 11

Phe Ser Arg Ser Asp Gln Leu Lys Arg
1               5

<210> SEQ ID NO 12
<211> LENGTH: 9
<212> TYPE: PRT
<213> ORGANISM: Homo sapiens

<400> SEQUENCE: 12

Ser Asp Gln Leu Lys Arg His Gln Arg
1               5

<210> SEQ ID NO 13
<211> LENGTH: 9
<212> TYPE: PRT
<213> ORGANISM: Homo sapiens

<400> SEQUENCE: 13

Thr Ser Glu Lys Pro Phe Ser Cys Arg
1               5

<210> SEQ ID NO 14
<211> LENGTH: 9
<212> TYPE: PRT
<213> ORGANISM: Homo sapiens

<400> SEQUENCE: 14

Pro Ile Leu Cys Gly Ala Gln Tyr Arg
1               5

<210> SEQ ID NO 15
<211> LENGTH: 9
<212> TYPE: PRT
<213> ORGANISM: Homo sapiens

<400> SEQUENCE: 15

Ser Ala Ser Glu Thr Ser Glu Lys Arg
1               5

<210> SEQ ID NO 16
<211> LENGTH: 9
<212> TYPE: PRT
<213> ORGANISM: Homo sapiens

<400> SEQUENCE: 16

Ser His Leu Gln Met His Ser Arg Lys
1               5

<210> SEQ ID NO 17
<211> LENGTH: 9
```

```
<212> TYPE: PRT
<213> ORGANISM: Homo sapiens

<400> SEQUENCE: 17

Thr Gly Val Lys Pro Phe Gln Cys Lys
1               5

<210> SEQ ID NO 18
<211> LENGTH: 9
<212> TYPE: PRT
<213> ORGANISM: Homo sapiens

<400> SEQUENCE: 18

Ser Leu Gly Glu Gln Gln Tyr Ser Val
1               5

<210> SEQ ID NO 19
<211> LENGTH: 9
<212> TYPE: PRT
<213> ORGANISM: Homo sapiens

<400> SEQUENCE: 19

Cys Tyr Thr Trp Asn Gln Met Asn Leu
1               5

<210> SEQ ID NO 20
<211> LENGTH: 9
<212> TYPE: PRT
<213> ORGANISM: Homo sapiens

<400> SEQUENCE: 20

Phe Leu Gly Glu Gln Gln Tyr Ser Val
1               5

<210> SEQ ID NO 21
<211> LENGTH: 9
<212> TYPE: PRT
<213> ORGANISM: Homo sapiens

<400> SEQUENCE: 21

Ser Met Gly Glu Gln Gln Tyr Ser Val
1               5

<210> SEQ ID NO 22
<211> LENGTH: 9
<212> TYPE: PRT
<213> ORGANISM: Homo sapiens

<400> SEQUENCE: 22

Ser Leu Met Glu Gln Gln Tyr Ser Val
1               5

<210> SEQ ID NO 23
<211> LENGTH: 9
<212> TYPE: PRT
<213> ORGANISM: Homo sapiens

<400> SEQUENCE: 23

Phe Met Phe Pro Asn Ala Pro Tyr Leu
1               5

<210> SEQ ID NO 24
<211> LENGTH: 9
<212> TYPE: PRT
<213> ORGANISM: Homo sapiens
```

```
<400> SEQUENCE: 24

Arg Leu Phe Pro Asn Ala Pro Tyr Leu
1               5

<210> SEQ ID NO 25
<211> LENGTH: 9
<212> TYPE: PRT
<213> ORGANISM: Homo sapiens

<400> SEQUENCE: 25

Arg Met Met Pro Asn Ala Pro Tyr Leu
1               5

<210> SEQ ID NO 26
<211> LENGTH: 9
<212> TYPE: PRT
<213> ORGANISM: Homo sapiens

<400> SEQUENCE: 26

Arg Met Phe Pro Asn Ala Pro Tyr Val
1               5

<210> SEQ ID NO 27
<211> LENGTH: 18
<212> TYPE: PRT
<213> ORGANISM: Homo sapiens

<400> SEQUENCE: 27

Ala Pro Val Leu Asp Phe Ala Pro Pro Gly Ala Ser Ala Tyr Gly Ser
1               5                   10                  15

Leu Gly

<210> SEQ ID NO 28
<211> LENGTH: 17
<212> TYPE: PRT
<213> ORGANISM: Homo sapiens

<400> SEQUENCE: 28

Glu Gln Cys Leu Ser Ala Phe Thr Val His Phe Ser Gly Gln Phe Thr
1               5                   10                  15

Gly

<210> SEQ ID NO 29
<211> LENGTH: 15
<212> TYPE: PRT
<213> ORGANISM: Homo sapiens

<400> SEQUENCE: 29

Pro Asn His Ser Phe Lys His Glu Asp Pro Met Gly Gln Gln Gly
1               5                   10                  15

<210> SEQ ID NO 30
<211> LENGTH: 19
<212> TYPE: PRT
<213> ORGANISM: Homo sapiens

<400> SEQUENCE: 30

Asn Leu Tyr Gln Met Thr Ser Gln Leu Glu Cys Met Thr Trp Asn Gln
1               5                   10                  15

Met Asn Leu
```

```
<210> SEQ ID NO 31
<211> LENGTH: 19
<212> TYPE: PRT
<213> ORGANISM: Homo sapiens

<400> SEQUENCE: 31

Phe Arg Gly Ile Gln Asp Val Arg Arg Val Pro Gly Val Ala Pro Thr
1               5                   10                  15

Leu Val Arg

<210> SEQ ID NO 32
<211> LENGTH: 16
<212> TYPE: PRT
<213> ORGANISM: Homo sapiens

<400> SEQUENCE: 32

Lys Arg Tyr Phe Lys Leu Ser His Leu Gln Met His Ser Arg Lys His
1               5                   10                  15

<210> SEQ ID NO 33
<211> LENGTH: 9
<212> TYPE: PRT
<213> ORGANISM: Homo sapiens

<400> SEQUENCE: 33

Asp Leu Asn Ala Leu Leu Pro Ala Val
1               5

<210> SEQ ID NO 34
<211> LENGTH: 9
<212> TYPE: PRT
<213> ORGANISM: Homo sapiens

<400> SEQUENCE: 34

Asp Gln Leu Lys Arg His Gln Arg Arg
1               5

<210> SEQ ID NO 35
<211> LENGTH: 9
<212> TYPE: PRT
<213> ORGANISM: Homo sapiens

<400> SEQUENCE: 35

Ala Ala Gly Ser Ser Ser Ser Val Lys
1               5

<210> SEQ ID NO 36
<211> LENGTH: 9
<212> TYPE: PRT
<213> ORGANISM: Homo sapiens

<400> SEQUENCE: 36

Arg Ser Ala Ser Glu Thr Ser Glu Lys
1               5

<210> SEQ ID NO 37
<211> LENGTH: 9
<212> TYPE: PRT
<213> ORGANISM: Homo sapiens

<400> SEQUENCE: 37

Lys Thr Cys Gln Arg Lys Phe Ser Arg
1               5
```

```
<210> SEQ ID NO 38
<211> LENGTH: 9
<212> TYPE: PRT
<213> ORGANISM: Homo sapiens

<400> SEQUENCE: 38

Ser Cys Arg Trp Pro Ser Cys Gln Lys
1               5

<210> SEQ ID NO 39
<211> LENGTH: 9
<212> TYPE: PRT
<213> ORGANISM: Homo sapiens

<400> SEQUENCE: 39

Asn Met His Gln Arg Asn Met Thr Lys
1               5

<210> SEQ ID NO 40
<211> LENGTH: 449
<212> TYPE: PRT
<213> ORGANISM: Homo sapiens

<400> SEQUENCE: 40

Met Gly Ser Asp Val Arg Asp Leu Asn Ala Leu Leu Pro Ala Val Pro
1               5                   10                  15

Ser Leu Gly Gly Gly Gly Gly Cys Ala Leu Pro Val Ser Gly Ala Ala
            20                  25                  30

Gln Trp Ala Pro Val Leu Asp Phe Ala Pro Pro Gly Ala Ser Ala Tyr
        35                  40                  45

Gly Ser Leu Gly Gly Pro Ala Pro Pro Ala Pro Pro Pro Pro
    50                  55                  60

Pro Pro Pro Pro His Ser Phe Ile Lys Gln Glu Pro Ser Trp Gly Gly
65                  70                  75                  80

Ala Glu Pro His Glu Glu Gln Cys Leu Ser Ala Phe Thr Val His Phe
                85                  90                  95

Ser Gly Gln Phe Thr Gly Thr Ala Gly Ala Cys Arg Tyr Gly Pro Phe
            100                 105                 110

Gly Pro Pro Pro Pro Ser Gln Ala Ser Ser Gly Gln Ala Arg Met Phe
        115                 120                 125

Pro Asn Ala Pro Tyr Leu Pro Ser Cys Leu Glu Ser Gln Pro Ala Ile
    130                 135                 140

Arg Asn Gln Gly Tyr Ser Thr Val Thr Phe Asp Gly Thr Pro Ser Tyr
145                 150                 155                 160

Gly His Thr Pro Ser His His Ala Ala Gln Phe Pro Asn His Ser Phe
                165                 170                 175

Lys His Glu Asp Pro Met Gly Gln Gln Gly Ser Leu Gly Glu Gln Gln
            180                 185                 190

Tyr Ser Val Pro Pro Pro Val Tyr Gly Cys His Thr Pro Thr Asp Ser
        195                 200                 205

Cys Thr Gly Ser Gln Ala Leu Leu Leu Arg Thr Pro Tyr Ser Ser Asp
    210                 215                 220

Asn Leu Tyr Gln Met Thr Ser Gln Leu Glu Cys Met Thr Trp Asn Gln
225                 230                 235                 240

Met Asn Leu Gly Ala Thr Leu Lys Gly Val Ala Ala Gly Ser Ser Ser
                245                 250                 255

Ser Val Lys Trp Thr Glu Gly Gln Ser Asn His Ser Thr Gly Tyr Glu
            260                 265                 270
```

```
Ser Asp Asn His Thr Thr Pro Ile Leu Cys Gly Ala Gln Tyr Arg Ile
        275                 280                 285

His Thr His Gly Val Phe Arg Gly Ile Gln Asp Val Arg Arg Val Pro
    290                 295                 300

Gly Val Ala Pro Thr Leu Val Arg Ser Ala Ser Glu Thr Ser Glu Lys
305                 310                 315                 320

Arg Pro Phe Met Cys Ala Tyr Pro Gly Cys Asn Lys Arg Tyr Phe Lys
                325                 330                 335

Leu Ser His Leu Gln Met His Ser Arg Lys His Thr Gly Glu Lys Pro
            340                 345                 350

Tyr Gln Cys Asp Phe Lys Asp Cys Glu Arg Arg Phe Ser Arg Ser Asp
        355                 360                 365

Gln Leu Lys Arg His Gln Arg Arg His Thr Gly Val Lys Pro Phe Gln
    370                 375                 380

Cys Lys Thr Cys Gln Arg Lys Phe Ser Arg Ser Asp His Leu Lys Thr
385                 390                 395                 400

His Thr Arg Thr His Thr Gly Lys Thr Ser Glu Lys Pro Phe Ser Cys
                405                 410                 415

Arg Trp Pro Ser Cys Gln Lys Lys Phe Ala Arg Ser Asp Glu Leu Val
            420                 425                 430

Arg His His Asn Met His Gln Arg Asn Met Thr Lys Leu Gln Leu Ala
        435                 440                 445

Leu
```

IMMUNOTHERAPY FOR ANGIOGENIC DISEASE

CROSS REFERENCE TO RELATED APPLICATIONS

The present application is a divisional of U.S. application Ser. No. 15/534,895, filed on Jun. 9, 2017, which is a 35 U.S.C. § 371 national stage patent application of International patent application PCT/JP2015/084709, filed on Dec. 10, 2015, the text of which is incorporated by reference, and claims the benefit of the filing date of Japanese application no. 2014-251208, filed on Dec. 11, 2014, the text of which is also incorporated by reference.

TECHNICAL FIELD

The present invention relates to immunotherapy for angiogenic diseases.

BACKGROUND ART

For angiogenic diseases such as various types of cancers, multiple myeloma, articular rheumatism, psoriasis, intraocular angiogenic diseases such as wet-type age-related macular degeneration, atherosclerotic plaque, vascular malformation, vascular agglutination, ovarian hypertrophy syndrome, polycystic ovary, granuloma, angioma, a hypertrophic scar, keloid, scleroderma, verruca, treatments are carried out using protamine, a combination of a steroid and heparin, a combination of a steroid and hexuronyl hexosaminoglycan sulfate, mitoxantrone, endostatin, a heparin-binding fragment of fibronectin, a prostaglandin synthetase inhibitor, y interferon, a gold compound, lymphotoxin, D-penicillamine, a combination of a steroid and ß-cyclodextrin tetradecasulfate, a protease inhibitor, methotrexate, interferon α-2a, an anti-VEGF drug, and the like.

Typical types of angiogenic diseases include intraocular angiogenic diseases such as wet-type age-related macular degeneration. A common method of treatment for intraocular angiogenic diseases uses an anti-VEGF drug as an intraocular injection. However, the method of treatment using an anti-VEGF drug takes a lot of money, needs repeated injections regularly, provides a great deal of psychological fear to patients of insertion of injection needles into their eye. Furthermore, there is a great risk of serious complications such as intraocular infections with great difficulty in treatment, endophthalmitis caused by stimulation of injection, and the like, and induction of retinal detachment. Further, there is a report that eyesight is improved for a certain period of time by a treatment using anti-VEGF drug in most cases, whereas the eyesight is worsened again in the long term even with continued treatment. That is, although an anti-VEGF drug used in the present treatment costs a lot, it has a danger, and thus sufficient treatment satisfaction is not necessarily achieved in view of its effects. Other treatments include surgical methods such as photodynamic therapy, laser photocoagulation, and neovascular extraction, however these methods have problems also in terms of costs and treatment satisfaction, have high invasiveness, and sometimes require hospitalization. Consequently, no conventional method of treatment for intraocular angiogenic diseases has been satisfactory yet, and thus it is considered that many problems to be overcome in the present treatments.

Recently, it was reported that a WT1 protein, which is a cancer antigenic protein, is also developed in blood vessels of cancer tissues (Non-Patent Literature 1: N. Wagner et al. Oncogene (2008) 27, 3662-3672).

There have already been many reports on experiments using a cancer antigen peptide as a cancer vaccine, however, there was no report on treatment and prevention of angiogenic diseases using a cancer antigen peptide as a vaccine.

Under the above circumstances, a novel complete curative therapy for angiogenic disease is desired.

CITATION LIST

Non-Patent Literature

Non-Patent Literature 1: N. Wagner et al. Oncogene (2008) 27, 3662-3672

SUMMARY OF INVENTION

Problems to be Solved

An object of the present invention is to provide a novel preparation for treatment and prevention of angiogenic diseases. Further, it is also an object of the present invention to provide a minimally invasive preparation which can be self-administered by the patient with a relatively low cost.

Means to Solve Problems

The present inventors, after pursuing a diligent study to solve the problems mentioned above, have found that angiogenic diseases can be treated or prevented by using a cancer antigen peptide as a vaccine. Further, the present inventors also have found that angiogenic diseases can be treated by systemic administration of a WT1 peptide. The present inventors have completed the present invention based on the findings.

Accordingly, the present invention provides the following.

(1) A pharmaceutical composition containing a cancer antigen peptide for any of treatment and prevention, or for both treatment and prevention of an angiogenic disease.

(2) A pharmaceutical composition containing antigen presentation cells, killer T cells, or helper T cells induced or activated with a cancer antigen peptide for any of treatment and prevention, or for both treatment and prevention of angiogenic disease.

(3) The pharmaceutical composition according to (1) or (2), wherein the cancer antigen peptide is a WT1 peptide or variant WT1 peptide.

(4) The pharmaceutical composition according to (3), wherein the WT1 peptide or variant WT1 peptide has a binding ability to an HLA molecule.

(5) The pharmaceutical composition according to (3) or (4), wherein the WT1 peptide or variant WT1 peptide activates killer T cells or helper T cells.

(6) The pharmaceutical composition according to any of (3) to (5), wherein the WT1 peptide has a length of 7 to 30 amino acids.

(7) The pharmaceutical composition according to any of (3) to (6), wherein the WT1 peptide comprises the following amino acid sequence:
  (a) any of the amino acid sequence represented by SEQ ID NO: 1 to SEQ ID NO: 39, or
  (b) an amino acid sequence, wherein one or several amino acids are replaced, deleted, or added in the amino acid sequence according to the above-described (a).

(8) The pharmaceutical composition according to any of (3) to (7), wherein the WT1 peptide comprises the following amino acid sequence:
(a) Arg Met Phe Pro Asn Ala Pro Tyr Leu (SEQ ID NO: 1),
(b) Cys Tyr Thr Trp Asn Gln Met Asn Leu (SEQ ID NO: 19),
(c) Ala Pro Val Leu Asp Phe Ala Pro Pro Gly Ala Ser Ala Tyr Gly Ser Leu Gly (SEQ ID NO: 27),
(d) Lys Arg Tyr Phe Lys Leu Ser His Leu Gln Met His Ser Arg Lys His (SEQ ID NO: 32), or
(e) an amino acid sequence, wherein one or several amino acids are replaced, deleted, or added in any of the amino acid sequences according to (a) to (d).

(9) The pharmaceutical composition according to any of (1) to (8), wherein the angiogenic disease is an intraocular angiogenic disease.

(10) The pharmaceutical composition according to (9), wherein the intraocular angiogenic disease is selected from the group consisting of wet-type age-related macular degeneration, myopic macular degeneration, angioid streaks, central serous chorioretinopathy, various types of retinal pigment epitheliopathy, choroidal atrophy, choroideremia, choroidal osteoma, diabetic retinopathy, retinopathy of prematurity, rubeotic glaucoma, and corneal neovascularization.

(11) The pharmaceutical composition according to any of (1) to (10), which is administered by intracutaneous administration, percutaneous administration, or transmucosal administration.

(12) The pharmaceutical composition according to (1) to (11), which is used in combination with a drug for any of treatment and prevention, or for both treatment and prevention of an angiogenic disease.

Effects of Invention

The present invention provides a pharmaceutical composition containing a cancer antigen peptide for any of treatment and prevention, or for both treatment and prevention of an angiogenic disease. Further, the present invention provides a pharmaceutical composition containing antigen presentation cells, killer T cells, or helper T cells induced or activated with a cancer antigen peptide for any of treatment and prevention, or for both treatment and prevention of an angiogenic disease. The pharmaceutical composition according to the present invention is minimally invasive because systemic administration, such as intracutaneous administration, subcutaneous administration, percutaneous administration, and transmucosal administration, as well as topical administration are available. Further, the pharmaceutical composition according to the present invention can be self-administered by the patient. Furthermore, the pharmaceutical composition according to the present invention has a high therapeutic effect, and a high treatment satisfaction of patients. Moreover, when an intraocular angiogenic disease is treated with the pharmaceutical composition according to the present invention, treating or preventing effect on the other eye can also be expected.

DESCRIPTION OF EMBODIMENTS

In one aspect, the present invention relates to a pharmaceutical composition containing a cancer antigen peptide for any of treatment and prevention, or for both treatment and prevention of an angiogenic disease. The cancer antigen peptide is a part of cancer antigenic proteins. Various cancer antigenic proteins including WT1 are known. The cancer antigen peptide used in the pharmaceutical composition of the present invention can be one species, or can be two or more species. Whether a cancer antigen WT1 peptide exerts a therapeutic effect on angiogenic diseases in a subject or not depends on whether the cancer antigen peptide corresponds to an HLA type of the subject or not. Currently, with respect to many cancer antigen peptides, it is known that what cancer antigen peptide is compatible with a certain HLA type, and thus a cancer antigen peptide used in the present invention can be selected in accordance with an HLA type of a subject. Thus, two or more species of cancer antigen peptides can be used in a pharmaceutical composition of the present invention to adapt broader ranges of subjects. Various angiogenic diseases are also known. Examples of the angiogenic disease include, but are not limited to, various types of cancers, multiple myeloma, articular rheumatism, psoriasis, intraocular angiogenic diseases such as wet-type age-related macular degeneration, atherosclerotic plaque, vascular malformation, vascular agglutination, ovarian hypertrophy syndrome, polycystic ovary, granuloma, angioma, a hypertrophic scar, keloid, scleroderma, and verruca.

A cancer antigen peptide can be administered to a subject, or added to a sample such as blood taken from a subject to obtain antigen presentation cells presenting said cancer antigen peptide. The antigen presentation cells presenting a cancer antigen stimulate lymphocytes to induce or activate killer T cells or helper T cells. An effect of the cancer antigen peptide is derived from the antigen presentation cells, killer T cells, or helper T cells induced or activated as mentioned above. Accordingly, in another aspect, the present invention relates to a pharmaceutical composition containing antigen presentation cells, killer T cells, or helper T cells induced or activated with a cancer antigen peptide for any of treatment and prevention, or for both treatment and prevention of angiogenic disease. The antigen presentation cells, killer T cells, or helper T cells used in the above-mentioned pharmaceutical composition can be induced or activated with any cancer antigen peptide, for example, induced or activated with a WT1 peptide.

Typical types of angiogenic disease include intraocular angiogenic diseases. Further, widely used species of cancer antigen peptide include a WT1 peptide. Accordingly, in a further aspect, the present invention relates to a pharmaceutical composition containing a WT1 peptide or variant WT1 peptide for treatment of intraocular angiogenic diseases.

As used herein, a WT1 peptide refers to a partial peptide of a cancer antigenic protein WT1 encoded by WT1 gene (Wilms' tumor gene 1). An amino acid sequence of the cancer antigenic protein WT1 is represented by SEQ ID NO: 40. Thus, a WT1 peptide is a peptide consisting of a successive amino acid sequence included in the cancer antigenic protein WT1. A WT1 peptide is well-known to a person skilled in the art, and there are many reports specifically concerning cancer immunotherapy. A WT1 peptide can be produced by publicly known methods such as a genetic engineering procedure or a chemical synthesis method. Unless otherwise indicated, a WT1 peptide used herein refers to a peptide derived from a human cancer antigenic protein WT1.

A WT1 peptide used in the present invention can be a variant WT1 peptide consisting of an amino acid in which one or several amino acids are replaced, deleted, or added in the amino acid sequence of a WT1 peptide. The variant WT1 peptide can be a WT1 peptide having an artificially modified amino acid sequence (also called as a modified WT1 peptide), a WT1 peptide obtained by natural mutation, or a WT1 peptide having difference in an amino acid sequence due to animal species which is the origin of the WT1 peptide. As used herein, the variant WT1 peptide has a similar therapeutic effect on intraocular angiogenic diseases to that of a natural type WT1 peptide. Methods of replacing, deleting, or adding in an amino acid sequence known to a person skilled in the art include genetic engineering procedure and chemical methods, and thus a person skilled in the art can easily obtain a desired amino acid sequence. The term one or several refers to, for example, 1, 2, 3, 4, 5, 6, 7, 8, 9, or 10, preferably 1, 2, 3, 4, or 5, more preferably 1, 2, or 3. Furthermore preferably, the term one or several refers to 1 or 2.

The variant WT1 peptides include peptides having a modification of an amino acid residue in a WT1 peptide. Types of modification and methods for modification of an amino acid residue in a peptide are known to a person skilled in the art. As specific examples for modification, various substances such as an amino acid, a peptide, or their analogs can be bound to N-terminus and/or C-terminus of a WT1 peptide. The above-mentioned various substances can be substances for controlling solubility of a WT1 peptide of the present invention, increasing its stability (e.g., anti-protease activity), delivering a WT1 peptide of the present invention specifically to predetermined tissues/organs, or enhancing uptake efficiency of antigen presentation cells. On the other hand, the above-mentioned various substances can be made such that the various substances can be eliminated in vivo to provide a WT1 peptide.

As used herein, unless otherwise indicated, the term a WT1 peptide includes a variant WT1 peptide.

Length of a WT1 peptide used in the present invention is not specifically limited, however a WT1 peptide consisting of about 7 to about 30 amino acids is preferred. A preferred WT1 peptide has regularity of a sequence (motif) of an antigen peptide, which is bound to and presented by an HLA molecule, and has a binding ability to an HLA molecule. A binding ability to an HLA molecule can be analyzed by methods known in the art. Such methods include, for example, computer-based methods such as Rankpep, BIMAS, and SYFPEITHI, and a competitive binding assay with a known WT1 peptide having binding ability to an HLA molecule. Further, a preferred WT1 peptide activates killer T cells or helper T cells.

Many WT1 peptides activating killer T cells (herein called as a killer WT1 peptide) are publicly known. Generally, a preferred killer WT1 peptide has an amino acid sequence consisting of 7 to 12 amino acids. A more preferred killer WT1 peptide has an amino acid sequence consisting of 9 amino acids. Examples of killer WT1 peptides which can be used in the present invention include, but are not limited to, peptides comprising or consisting of the following amino acid sequences: Arg Met Phe Pro Asn Ala Pro Tyr Leu (SEQ ID NO: 1), Arg Tyr Pro Ser Cys Gln Lys Lys Phe (SEQ ID NO: 2), Arg Tyr Phe Pro Asn Ala Pro Tyr Leu (SEQ ID NO: 3), Ala Tyr Leu Pro Ala Val Pro Ser Leu (SEQ ID NO: 4), Asn Tyr Met Asn Leu Gly Ala Thr Leu (SEQ ID NO: 5), Asp Gln Leu Lys Arg His Gln Arg Arg (SEQ ID NO: 6), Val Thr Phe Asp Gly Thr Pro Ser Tyr (SEQ ID NO: 7), Gln Gly Ser Leu Gly Glu Gln Gln Tyr (SEQ ID NO: 8), Cys Met Thr Trp Asn Gln Met Asn Leu (SEQ ID NO: 9), Leu Ser His Leu Gln Met His Ser Arg (SEQ ID NO: 10), Phe Ser Arg Ser Asp Gln Leu Lys Arg (SEQ ID NO: 11), Ser Asp Gln Leu Lys Arg His Gln Arg (SEQ ID NO: 12), Thr Ser Glu Lys Pro Phe Ser Cys Arg (SEQ ID NO: 13), Pro Ile Leu Cys Gly Ala Gln Tyr Arg (SEQ ID NO: 14), Ser Ala Ser Glu Thr Ser Glu Lys Arg (SEQ ID NO: 15), Ser His Leu Gln Met His Ser Arg Lys (SEQ ID NO: 16), Thr Gly Val Lys Pro Phe Gln Cys Lys (SEQ ID NO: 17), Ser Leu Gly Glu Gln Gln Tyr Ser Val (SEQ ID NO: 18), Cys Tyr Thr Trp Asn Gln Met Asn Leu (SEQ ID NO: 19), Phe Leu Gly Glu Gln Gln Tyr Ser Val (SEQ ID NO: 20), Ser Met Gly Glu Gln Gln Tyr Ser Val (SEQ ID NO: 21), Ser Leu Met Glu Gln Gln Tyr Ser Val (SEQ ID NO: 22), Phe Met Phe Pro Asn Ala Pro Tyr Leu (SEQ ID NO: 23), Arg Leu Phe Pro Asn Ala Pro Tyr Leu (SEQ ID NO: 24), Arg Met Met Pro Asn Ala Pro Tyr Leu (SEQ ID NO: 25), or Arg Met Phe Pro Asn Ala Pro Tyr Val (SEQ ID NO: 26), and variant WT1 peptides of the above-mentioned peptides. Other examples of killer WT1 peptides include, but are not limited to, those disclosed in International Publication No. WO 2000/018795 (incorporated herein by reference in its entirety).

Many WT1 peptides activating helper T cells (herein called as a helper WT1 peptide) are publicly known. Generally, a preferred helper WT1 peptide has an amino acid sequence consisting of 10 to 25 amino acids. A more preferred helper WT1 peptide has an amino acid sequence consisting of 13 to 20 amino acids. Examples of helper WT1 peptides which can be used in the present invention include, but are not limited to, peptides comprising or consisting of the following amino acid sequences: Ala Pro Val Leu Asp Phe Ala Pro Pro Gly Ala Ser Ala Tyr Gly Ser Leu Gly (SEQ ID NO: 27), Glu Gln Cys Leu Ser Ala Phe Thr Val His Phe Ser Gly Gln Phe Thr Gly (SEQ ID NO: 28), Pro Asn His Ser Phe Lys His Glu Asp Pro Met Gly Gln Gln Gly (SEQ ID NO: 29), Asn Leu Tyr Gln Met Thr Ser Gln Leu Glu Cys Met Thr Trp Asn Gln Met Asn Leu (SEQ ID NO: 30), Phe Arg Gly Ile Gln Asp Val Arg Arg Val Pro Gly Val Ala Pro Thr Leu Val Arg (SEQ ID NO: 31), or Lys Arg Tyr Phe Lys Leu Ser His Leu Gln Met His Ser Arg Lys His (SEQ ID NO: 32), and variant WT1 peptides of the above-mentioned peptides.

A WT1 peptide used in a pharmaceutical composition of the present invention can be one species, or two or more species. Further, a WT1 peptide used in the pharmaceutical composition of the present invention can be a killer WT1 peptide or helper WT1 peptide, or a killer WT1 peptide and a helper WT1 peptide can be mixed for use in the pharmaceutical composition.

In the present invention, a dimer of WT1 peptides can be used. The dimer of WT1 peptides can be obtained by forming a disulfide bond between two WT1 peptides having cysteine residues.

A WT1 peptide used in a pharmaceutical composition of the present invention can be one species, or can be two or more species. Whether a WT1 peptide exerts a therapeutic effect on intraocular angiogenic diseases in a subject or not depends on whether the WT1 peptide corresponds to HLA type of the subject or not. Currently, with respect to many WT1 peptides, it is known that what WT1 peptide is compatible with a certain HLA type, and thus a WT1 peptide used in the present invention can be selected in accordance with an HLA type of a subject. Further, two or more species of WT1 peptides can be used in a pharmaceutical composition of the present invention to adapt broader ranges of subjects.

For example, when a subject is HLA-A*0201-positive, examples of preferred WT1 peptides used in a pharmaceutical composition of the present invention include, but are not limited to, peptides comprising or consisting of the following amino acid sequences: Asp Leu Asn Ala Leu Leu Pro Ala Val (SEQ ID NO: 33), Arg Met Phe Pro Asn Ala Pro Tyr Leu (SEQ ID NO: 1), or Ser Leu Gly Glu Gln Gln Tyr Ser Val (SEQ ID NO: 18), and peptides comprising or consisting of an amino acid sequence in which one or several amino acids are replaced, deleted, or added in the amino acid sequence mentioned above.

For example, when a subject is HLA-A*2601-positive, examples include, but are not limited to, peptides comprising or consisting of the following amino acid sequences: Val Thr Phe Asp Gly Thr Pro Ser Tyr (SEQ ID NO: 7), Gln Gly Ser Leu Gly Glu Gln Gln Tyr (SEQ ID NO: 8), or Asp Gln Leu Lys Arg His Gln Arg Arg (SEQ ID NO: 34), and peptides comprising or consisting of an amino acid sequence in which one or several amino acids are replaced, deleted, or added in the amino acid sequence mentioned above.

For example, when a subject is HLA-A*3303-positive, examples include, but are not limited to, peptides comprising or consisting of the following amino acid sequences: Leu Ser His Leu Gln Met His Ser Arg (SEQ ID NO: 10), Phe Ser Arg Ser Asp Gln Leu Lys Arg (SEQ ID NO: 11), Ser Asp Gln Leu Lys Arg His Gln Arg (SEQ ID NO: 12), or Thr Ser Glu Lys Pro Phe Ser Cys Arg (SEQ ID NO: 13), and peptides comprising or consisting of an amino acid sequence in which one or several amino acids are replaced, deleted, or added in the amino acid sequence mentioned above.

For example, when a subject is HLA-A*1101-positive, examples include, but are not limited to, peptides comprising or consisting of the following amino acid sequences: Ala Ala Gly Ser Ser Ser Ser Val Lys (SEQ ID NO: 35), Pro Ile Leu Cys Gly Ala Gln Tyr Arg (SEQ ID NO: 14), Arg Ser Ala Ser Glu Thr Ser Glu Lys (SEQ ID NO: 36), Ser Ala Ser Glu Thr Ser Glu Lys Pro (SEQ ID NO: 15), Ser His Leu Gln Met His Ser Arg Lys (SEQ ID NO: 16), Thr Gly Val Lys Pro Phe Gln Cys Lys (SEQ ID NO: 17), Lys Thr Cys Gln Arg Lys Phe Ser Arg (SEQ ID NO: 37), Ser Cys Arg Trp Pro Ser Cys Gln Lys (SEQ ID NO: 38), or Asn Met His Gln Arg Asn Met Thr Lys (SEQ ID NO: 39), and peptides comprising or consisting of an amino acid sequence in which one or several amino acids are replaced, deleted, or added in the amino acid sequence mentioned above.

For example, when a subject is HLA-A*2402-positive, examples include, but are not limited to, peptides comprising or consisting of the following amino acid sequences: Cys Met Thr Trp Asn Gln Met Asn Leu (SEQ ID NO: 9), or Cys Tyr Thr Trp Asn Gln Met Asn Leu (SEQ ID NO: 19), a dimer of peptides comprising or consisting of amino acid sequence of SEQ ID NO: 9, a cystine form of peptides comprising or consisting of amino acid sequence of SEQ ID NO: 9, and peptides comprising or consisting of an amino acid sequence in which one or several amino acids are replaced, deleted, or added in the amino acid sequence mentioned above.

For example, when a subject is HLA-DRB1-positive, HLA-DRB3-positive, HLA-DRB4-positive, HLA-DRB5-positive, HLA-DPB1-positive, or HLA-DQB1-positive, examples include, but are not limited to, peptides comprising or consisting of the following amino acid sequences: Ala Pro Val Leu Asp Phe Ala Pro Pro Gly Ala Ser Ala Tyr Gly Ser Leu Gly (SEQ ID NO: 27), Glu Gln Cys Leu Ser Ala Phe Thr Val His Phe Ser Gly Gln Phe Thr Gly (SEQ ID NO: 28), Pro Asn His Ser Phe Lys His Glu Asp Pro Met Gly Gln Gln Gly (SEQ ID NO: 29), Asn Leu Tyr Gln Met Thr Ser Gln Leu Glu Cys Met Thr Trp Asn Gln Met Asn Leu (SEQ ID NO: 30), Phe Arg Gly Ile Gln Asp Val Arg Arg Val Pro Gly Val Ala Pro Thr Leu Val Arg (SEQ ID NO: 31), or Lys Arg Tyr Phe Lys Leu Ser His Leu Gln Met His Ser Arg Lys His (SEQ ID NO: 32), and peptides comprising or consisting of an amino acid sequence in which one or several amino acids are replaced, deleted, or added in the amino acid sequence mentioned above.

As an active ingredient in a pharmaceutical composition of the present invention, a polynucleotide encoding a WT1 peptide can be used. A base sequence of the polynucleotide can be determined based on the amino acid sequence of the WT1 peptide. The polynucleotide can be manufactured by, for example, publicly known DNA synthesis method or RNA synthesis method, such as a chemical synthesis method, PCR method, and the like.

The pharmaceutical composition of the present invention, and a drug used for any of treatment and prevention or for both treatment and prevention of angiogenic disease can be used in combination. Examples of the drug used for any of treatment and prevention or both treatment and prevention of angiogenic disease include, but are not limited to, bevacizumab, cetuximab, panitumumab, and the like. Examples of the drug used for any of treatment and prevention or both treatment and prevention of intraocular angiogenic diseases include, but are not limited to, vascular endothelial growth factor inhibitors, such as aflibercept, pegaptanib sodium, ranibizumab, and the like.

Intraocular angiogenic diseases which can be treated with a pharmaceutical composition of the present invention include, but are not limited to, wet-type age-related macular degeneration, myopic macular degeneration, angioid streaks, central serous chorioretinopathy, various types of retinal pigment epitheliopathy, choroidal atrophy, choroideremia, choroidal osteoma, diabetic retinopathy, retinopathy of prematurity, rubeotic glaucoma, and corneal neovascularization.

Routes of administration for a pharmaceutical composition of the present invention are not specifically limited, however examples of preferred route of administration include intracutaneous administration, subcutaneous administration, percutaneous administration, and transmucosal administration, such as eye drops, nasal spray, and sublingual.

Dosage forms of a pharmaceutical composition of the present invention are not specifically limited, and examples of dosage form include a liquid medicine for injection, an eye drop liquid medicine, a liquid medicine for nasal spray, a lotion, creams, a patch, sublingual tablet, and a troche. These dosage forms can be manufactured and administered by methods well-known to a person skilled in the art.

When a pharmaceutical composition of the present invention is used, the dose of a WT1 peptide can be appropriately changed based on consideration of types of WT1 peptides, route of administration, dosage form, types of disease, severity of diseases, state of health of a patient, and the like. In general, the dose of a WT1 peptide for adult is 0.1 μg/kg to 1 mg/kg daily. Further, types of WT1 peptides, route of administration, and dosage form can be appropriately changed. The pharmaceutical composition of the present invention can include a suitable adjuvant such as aluminum hydroxide in addition to a pharmaceutically acceptable carrier and a diluent. On the other hand, the pharmaceutical composition of the present invention can contain a WT1 peptide encapsulated in liposomes.

In another aspect, the present invention relates to use of a WT1 peptide for any of treatment and prevention or for both treatment and prevention of intraocular angiogenic diseases. In a further aspect, the present invention relates to use of a WT1 peptide for the manufacture of a medicament for any of treatment and prevention or for both treatment and prevention of intraocular angiogenic diseases. In still another aspect, the present invention relates to a method for any of treatment and prevention or for both treatment and prevention of intraocular angiogenic diseases characterized by administrating a WT1 peptide to a subject in need of any of treatment and prevention or both treatment and prevention of intraocular angiogenic diseases. The above description also applies to these aspects.

In further aspect, the present invention relates to a pharmaceutical composition containing antigen presentation cells, killer T cells, or helper T cells induced or activated with a WT1 peptide for any of treatment and prevention or for both treatment and prevention of intraocular angiogenic diseases. Further, the present invention relates to use of antigen presentation cells, killer T cells, or helper T cells induced or activated with a WT1 peptide for any of treatment and prevention or for both treatment and prevention of intraocular angiogenic diseases. Moreover, the present invention relates to use of antigen presentation cells, killer T cells, or helper T cells induced or activated with a WT1 peptide for the manufacture of a medicament for any of treatment and prevention or for both treatment and prevention of intraocular angiogenic diseases. In still another aspect, the present invention relates to a method for any of treatment and prevention or for both treatment and prevention of intraocular angiogenic diseases characterized by administering antigen presentation cells, killer T cells, or helper T cells induced or activated with a WT1 peptide to a subject in need of any of treatment and prevention or both treatment and prevention of intraocular angiogenic diseases. The above description also applies to these aspects.

Methods for inducing or activating antigen presentation cells, killer T cells or helper T cells are known to a person skilled in the art. In vivo, a WT1 peptide can be administered to a subject to induce or activate killer T cells and helper T cells. In vitro, for example, a sample containing lymphocytes derived from a subject can be reacted with a WT1 peptide-HLA molecule complex to obtain killer T cells. Further, for example, peripheral blood mononuclear cells derived from a subject can be cultured in the presence of a WT1 peptide to induce WT1-specific CTL from said peripheral blood mononuclear cells. Moreover, for example, immature antigen presentation cells derived from a subject can be cultured in the presence of a WT1 peptide to induce antigen presentation cells which present a WT1 peptide via an HLA molecule. The immature antigen presentation cells refer to cells which can mature into antigen presentation cells, and examples of the immature antigen presentation cells include immature dendritic cells. Further, for example, a WT1 peptide can be added to antigen presentation cells to activate helper T cells. Antigen presentation cells, killer T cells, or helper T cells used in a pharmaceutical composition of the present invention can be induced or activated with any WT1 peptide. Thus induced or activated antigen presentation cells, killer T cells, or helper T cells can be administered to a subject, preferably to a subject from which these cells were obtained to carry out treatment and prevention of intraocular angiogenic diseases.

The above description of treatment and/or prevention is mainly with respect to intraocular angiogenic diseases, however, the above description also applies to other angiogenic diseases.

The present invention is described below specifically and in more detail with reference to examples, but the examples should not be construed to limit the invention in any way.

EXAMPLE

Example 1

Demonstration of a therapeutic effect of a WT1 peptide vaccine using a mouse model of laser-induced choroid coat angiogenesis
1. Experimental Method
1-1. Test Substance Two species of WT1 peptides: $WT1_{126}$ (Arg Met Phe Pro Asn Ala Pro Tyr Leu (SEQ ID NO: 1)) and $WT1_{35}$ (Ala Pro Val Leu Asp Phe Ala Pro Pro Gly Ala Ser Ala Tyr Gly Ser Leu Gly (SEQ ID NO: 27)), were used as test substances.
1-2. Animal Used for Experiment Male C57BL/6J mice (provided by CLEA Japan, Inc.) were used. At the beginning of the experiment, the mice were 8 weeks old (body weight: about 20 to 25 g). The mice were free-fed with laboratory chow (manufactured by Oriental Yeast Co., Ltd.) and tap water. Six mice were used for each administration group.
1-3. Dose and Method of Administration As a WT1 peptide, $WT1_{126}$ or $WT1_{35}$ was dissolved in sterilized PBS so that the concentration of the solution was 22.7 mg/mL. The resultant was diluted to 0.227 or 2.27 mg/mL with sterilized PBS. The resultant WT1 solution and Montanide ISA51 VG were mixed so that the volume ratio was 1:1.27 to prepare emulsions of 0.1 μg/μL, 1 μg/μL, and 10 μg/μL. Each of the emulsions was intracutaneously administered at 10 μL/body. Administered doses were 1 μg/body, 10 μg/body, and 100 μg/body. Timing of administrations were on 15, 22, 29, and 36 days after photocoagulation.

Specifically, with respect to the mice of administration groups (groups 1 to 4) administered with the test substance (WT1 peptide), the administration was carried out through the following procedure.
(1) Grouping was carried out on the basis of area of fluorescence leakage on 14 days after the photocoagulation.
(2) Body weight measurement and general symptom observation were carried out 15, 22, 29, and 36 days after photocoagulation.
(3) Abdomen was shaved with hair clippers, and then intracutaneous administration was carried out using a 30G injection needle.

Constitutions of the experiment groups (6 animals/group) are summarized in Table 1.

TABLE 1

| Group number | Test substance | Route of administration |
|---|---|---|
| 1 | PBS | Intracutaneous |
| 2 | 1 μg/body $WT1_{126}$ or $WT1_{35}$ | |
| 3 | 10 μg/body $WT1_{126}$ or $WT1_{35}$ | |
| 4 | 100 μg/body $WT1_{126}$ or $WT1_{35}$ | |

1-4. Photocoagulation and Ocular Fundus Imaging

Procedure used was as follows.

(1) Body weight measurement and general symptom observation were carried out.
(2) Dilatation of pupils was carried out with Mydrin-P (manufactured by Santen Pharmaceutical Co., Ltd.), and then general anesthesia was performed by intramuscular administration at 1 mL/kg of a mixture of Ketalar injection and Celactal injection (7:1).
(3) Photocoagulation was carried out using Multi Color Laser Photocoagulator (red) (manufactured by NIDEK CO., LTD.) under the following coagulation conditions: spot size of 50 μm, output of 60 mW, and coagulation time of 0.1 second.
(4) A cover glass for tissue observation was used as a contact lens, and then 4 photocoagulations were carried out, provided that sporadic large retinal blood vessels in posterior ocular fundus were excluded.
(5) Ocular fundus imaging was carried out using Micron III (manufactured by Phoenix Research Labs) promptly after the photocoagulation.
(6) Eye drops of Hyalein ophthalmic solution were applied to both eyes.

1-5. Fluorescence Ocular Fundus Angiography

Procedure used was as follows.

(1) Body weight measurement and general symptom observation were carried out 14, 21, 28, 35, and 42 days after photocoagulation.
(2) Dilatation of pupils was carried out with Mydrin-P, and then general anesthesia was performed by intramuscular administration at 1 mL/kg of a mixture of Ketalar injection (manufactured by DAIICHI SANKYO COMPANY, LIMITED) and Celactal injection (manufactured by Bayer) (7:1).
(3) Fluorescite (Manufactured by Alcon, Inc.) was injected at 0.1 mL/kg via the tail vein, and then fluorescence ocular fundus angiography was carried out using Micron III.
(4) An area of fluorescence leakage was calculated using an image analysis software.

1-6. Summary of Observations, Measurements, Inspection Items, Etc.

Figure 1:
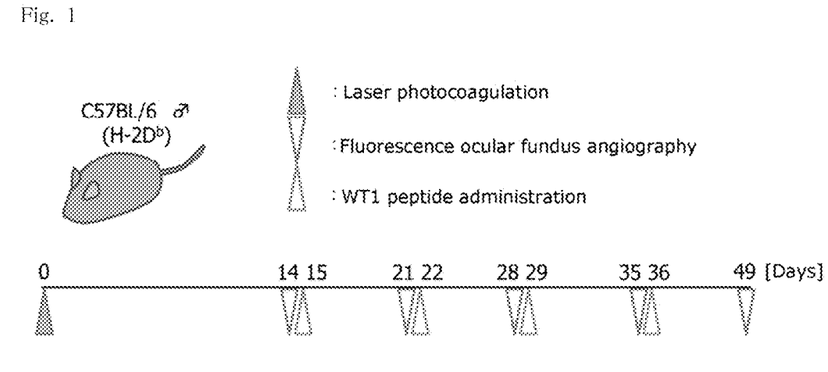
FIG. 1 is a scheme showing a summary of observations, measurements, inspection items, and the like in animal experiments.

FIG. 1 summarizes the description mentioned above.

1-7. Data Analysis

Microsoft EXCEL was used for data analysis, and the obtained results are shown as mean+/−standard deviation. EXSUS version 8.0.0 (SAS ver.9.3, CAC EXICARE Corporation) was used for a statistical analysis, and Dunnett type multigroup comparison (group 1 vs groups 2, 3, and 4) was selected to carry out a multiple comparison test. A significance level of <5% was used for all tests.

2. Results of Experiments

Figure 2:
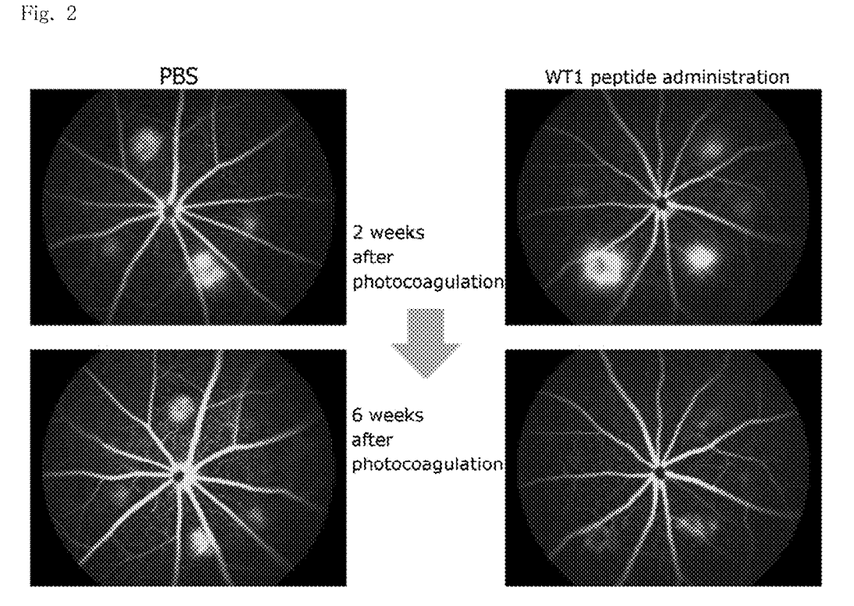
FIG. 2 is a typical fluorescein fluorescent ocular fundus image showing ocular fundus antiangiogenic effect of a WT1 peptide vaccine. Two pictures on the left show results of PBS intracutaneous administration (control), and two pictures on the right show results of intracutaneous administration with a WT1 peptide (WT1$_{126}$: Arg Met Phe Pro Asn Ala Pro Tyr Leu (SEQ ID NO: 1)).

Measurement results of angiogenesis by fluorescence ocular fundus angiography at 2 weeks after and at 6 weeks after the photocoagulation are shown in FIG. 2. The angiogenesis of the ocular fundus of the mice, which were administered with a WT1 peptide ($WT1_{126}$), at 6 weeks after the photocoagulation was significantly suppressed as compared to that of the mice in PBS administration group.

Figure 3:
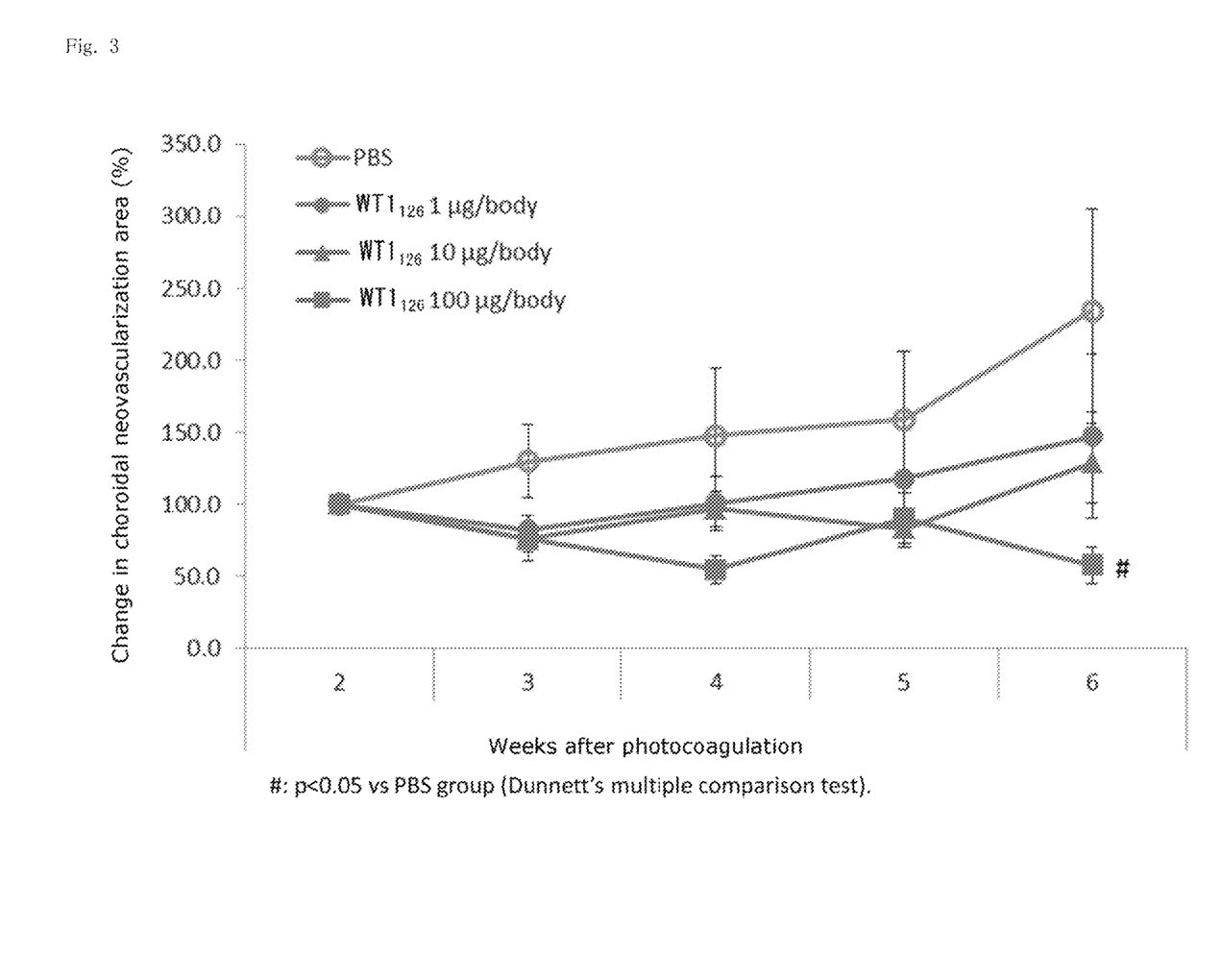
FIG. 3 is a graph showing changes of choroidal neovascular areas obtained by time-course analysis with intracutaneous administration at 1 μg/body, 10 μg/body, and 100 μg/body of a WT1 peptide (WT1$_{126}$: Arg Met Phe Pro Asn Ala Pro Tyr Leu (SEQ ID NO: 1)).
Figure 4:
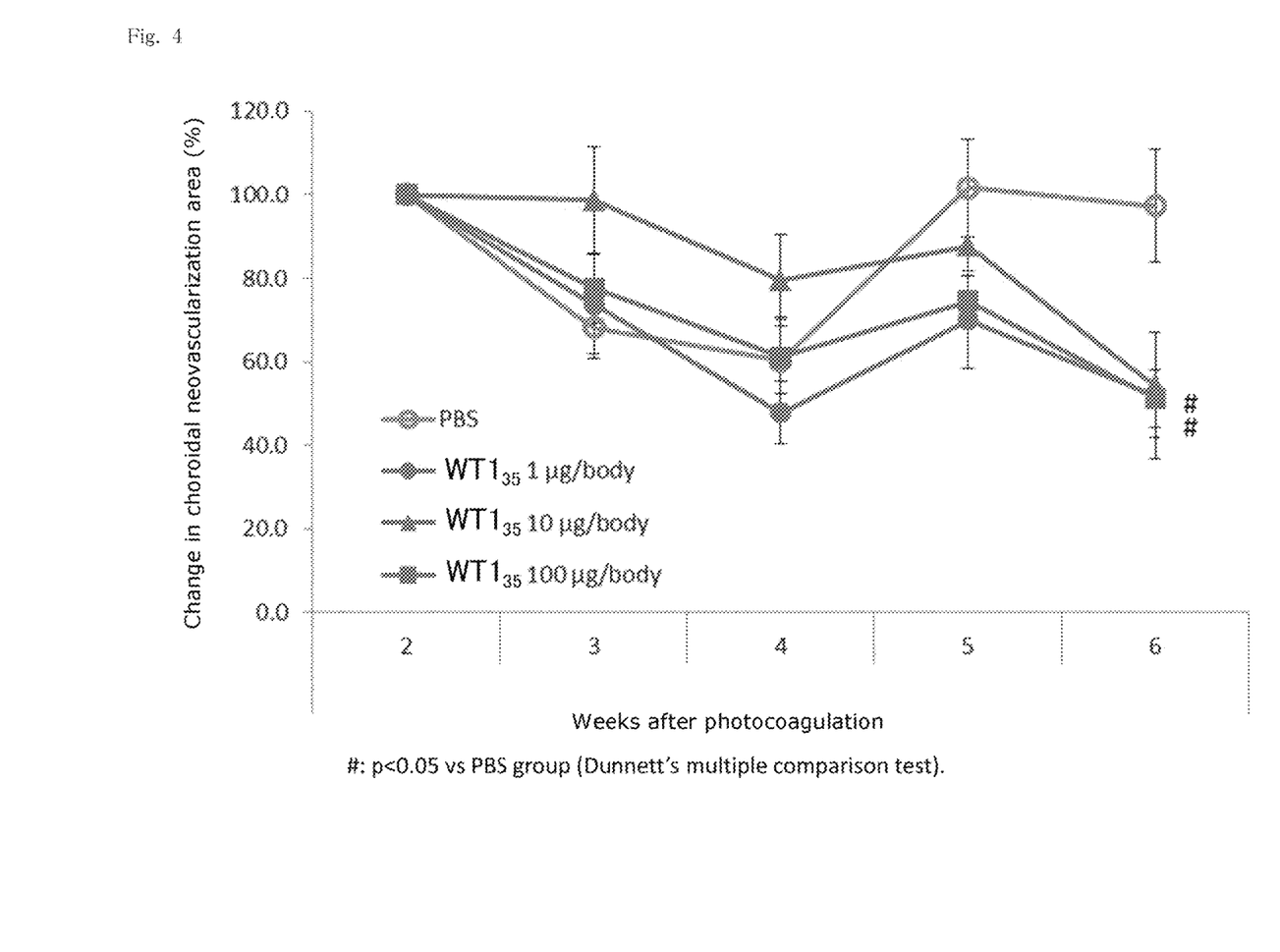
FIG. 4 is a graph showing changes of choroidal neovascular areas obtained by time-course analysis with intracutaneous administration at 1 μg/body, 10 μg/body, and 100 μg/body of a WT1 peptide (WT1$_{35}$: Ala Pro Val Leu Asp Phe Ala Pro Pro Gly Ala Ser Ala Tyr Gly Ser Leu Gly (SEQ ID NO: 27)).

Fluorescence ocular fundus angiography was carried out at 2 weeks, 3 weeks, 4 weeks, and 6 weeks after the photocoagulation to analyze time-dependent change of choroidal neovascular area. FIG. 3 shows data of mice administered with $WT1_{126}$, and FIG. 4 shows data of mice administered with $WT1_{35}$. Decrease in choroidal neovascular area with administration of a WT1 peptide was observed in mice with administration of either WT1 peptide.

In $WT1_{126}$ administration group, choroidal neovascular area was decreased with any applied dose of 1 μg/body, 10 μg/body, and 100 μg/body as compared to that of PBS administration group. Specifically, in the group administered with 100 μg/body of $WT1_{126}$, the decreasing effect was significant, that is, choroidal neovascular area at 6 weeks after the photocoagulation was reduced to about 50% of choroidal neovascular area at 2 weeks after the photocoagulation. On the other hand, in PBS administration group, choroidal neovascular area at 6 weeks after the photocoagulation was increased to about 230% of choroidal neovascular area at 2 weeks after the photocoagulation.

Also in $WT1_{35}$ administration group, decreasing trend in choroidal neovascular area was also observed with any applied dose of 1 μg/body, 10 μg/body, and 100 μg/body. Choroidal neovascular area at 6 weeks after the photocoagulation was reduced to about 50% of choroidal neovascular area at 2 weeks after the photocoagulation.

Example 2

Two species of WT1 peptides: $WT1_{235m}$ (Cys Tyr Thr Trp Asn Gln Met Asn Leu (SEQ ID NO: 19)) and $WT1_{332}$ (Lys Arg Tyr Phe Lys Leu Ser His Leu Gln Met His Ser Arg Lys His (SEQ ID NO: 32)) were used as test substances, and following setting of administration groups were provided to conduct an experiment in the same method and procedure as Example 1. The $WT1_{235m}$ was a peptide in which methionine in position 2 of $WT1_{235}$ (SEQ ID NO: 9) was replaced with tyrosine.

TABLE 2

| Group number | Test substance | Dose of administration | Volume of administration | Number of administration | Mouse strain Number of experiment |
|---|---|---|---|---|---|
| 1 | PBS | — | 10 μL/body | 1 (intracutaneously) | C57BL6 12 mice |
| 2 | $WT1_{235m}$ | 200 μg/body | 10 μL/body | 4 (intracutaneously) | CBF-1 12 mice |
| 3 | $WT1_{332}$ | 200 μg/body | 10 μL/body | 4 (intracutaneously) | CBF-1 12 mice |

Figure 5:
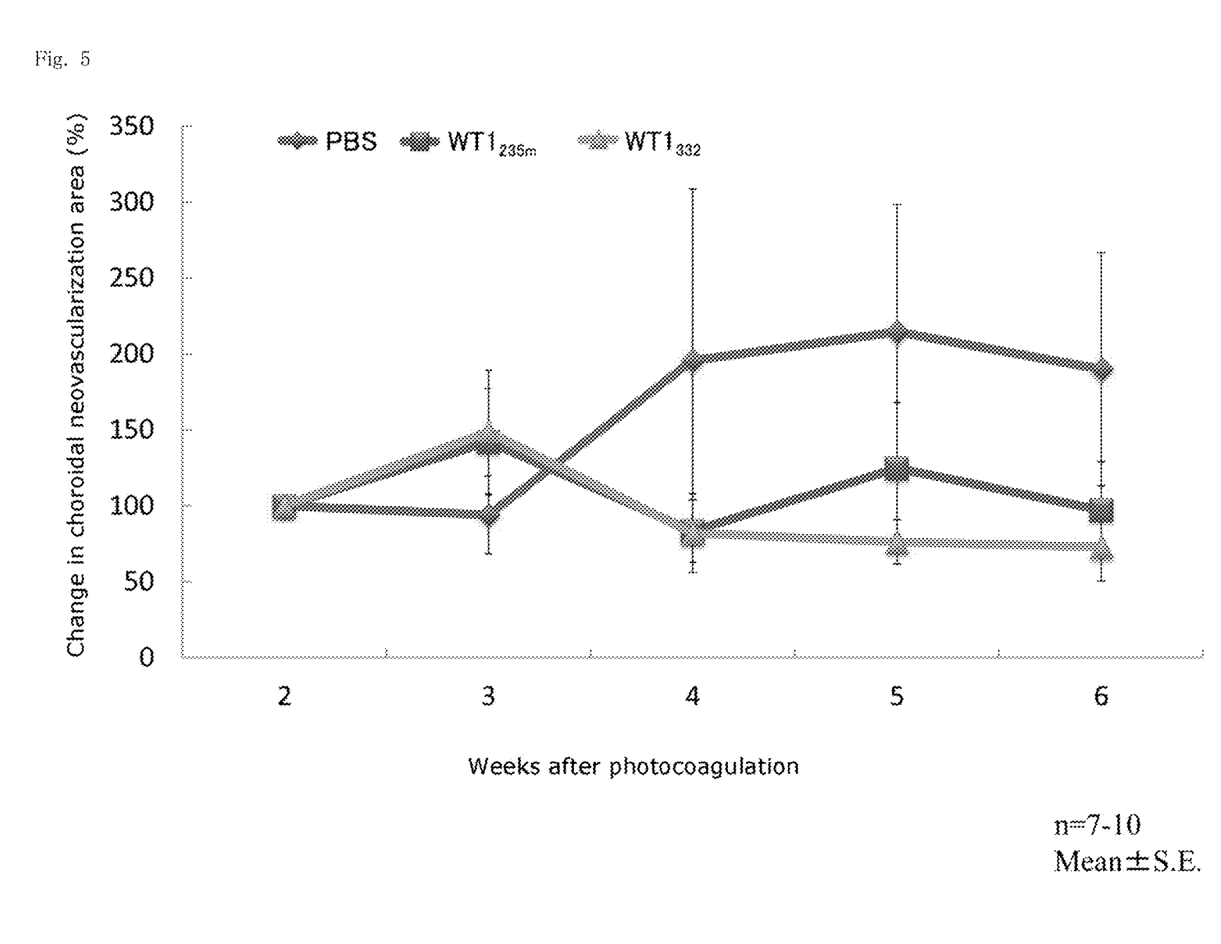
FIG. 5 is a graph showing changes of choroidal neovascular areas obtained by time-course analysis with intracutaneous administration at 200 μg/body of a WT1 peptide (WT1$_{235m}$: Cys Tyr Thr Trp Asn Gln Met Asn Leu (SEQ ID NO: 19), and WT1$_{332}$: Lys Arg Tyr Phe Lys Leu Ser His Leu Gln Met His Ser Arg Lys His (SEQ ID NO: 32)).

Fluorescence ocular fundus angiography was carried out at 2 weeks, 3 weeks, 4 weeks, 5 weeks, and 6 weeks after the photocoagulation to analyze time-dependent change of choroidal neovascular area. Results are shown in FIG. 5. Decrease in choroidal neovascular area with administration of a WT1 peptide was observed in mice with administration of either WT1 peptide of $WT1_{235m}$ or $WT1_{332}$ as compared to that of PBS administration group. In $WT1_{332}$ administration group, choroidal neovascular area at 6 weeks after the photocoagulation was reduced to about 70% of choroidal neovascular area at 2 weeks after the photocoagulation. In $WT1_{235m}$ administration group, increase in choroidal neovascular area was suppressed, that is, choroidal neovascular area at 6 weeks after the photocoagulation was the same as that at 2 weeks after the photocoagulation.

Example 3

Time-dependent change of choroidal neovascular area was analyzed when WT1 peptides ($WT1_{126}$, $WT1_{235m}$, and $WT1_{332}$) and Aflibercept were used in combination. Settings of administration groups were provided as follows (combination use groups: group 3, 4, and 5). Intravitreal administration of Aflibercept to the right eye was carried on the same day of laser application.

TABLE 3

| Group number | Administered substance | Dose of administration | Volume of administration | Number of administration | Mouse strain Number of experiment |
|---|---|---|---|---|---|
| 1 | PBS | — | 10 µL/body | 1 | C57BL6 12 mice |
| 2 | Aflibercept | 40 µg/eye | 1 µL/eye | 1 | C57BL6 12 mice |
| 3 | Aflibercept $WT1_{126}$ | 40 µg/eye 100 µg/body | 1 µL/eye 10 µL/body | 1 4 | C57BL6 12 mice |
| 4 | Aflibercept $WT1_{235m}$ | 40 µg/eye 200 µg/body | 1 µL/eye 10 µL/body | 1 4 | CBF-1 12 mice |
| 5 | Aflibercept $WT1_{332}$ | 40 µg/eye 200 µg/body | 1 µL/eye 10 µL/body | 1 4 | CBF-1 12 mice |

Figure 6:
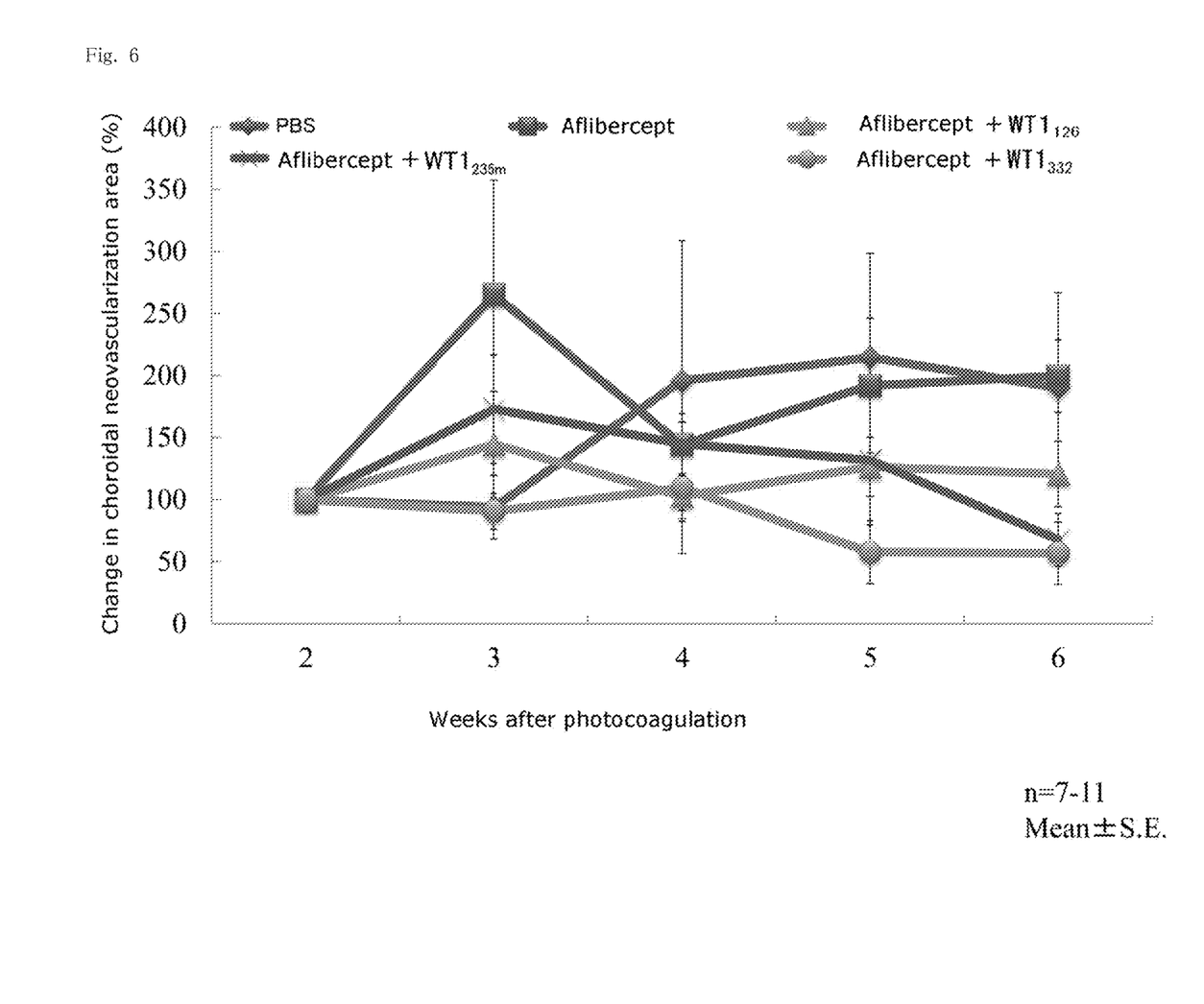
FIG. 6 is a graph showing changes of choroidal neovascular areas obtained by time-course analysis when WT1 peptides (WT1$_{126}$, WT1$_{235m}$, and WT1$_{332}$) and Aflibercept are used in combination.

Results are shown in FIG. 6. Decrease in choroidal neovascular area or suppression of increase in choroidal neovascular area was observed when a WT1 peptide and Aflibercept were used in combination, and thus a combined effect was confirmed.

According to the above-described results of experiments, it is confirmed that a WT1 peptide, which is a cancer antigen peptide, is effective in treatment for angiogenic disease.

INDUSTRIAL APPLICABILITY

The present invention provides a pharmaceutical composition containing a cancer antigen peptide for any of treatment and prevention, or for both treatment and prevention of an angiogenic disease, and thus can be used in specifically pharmaceutical field.

The invention claimed is:

1. A method for treating an intraocular angiogenic disease, comprising:
administering to a subject in need thereof a pharmaceutical composition comprising an antigen presentation cell, a killer T cell, or a helper T cell induced or activated with a WT1 peptide,
wherein the WT1 peptide has a length of 7 to 30 amino acids;
wherein the WT1 peptide comprises an amino acid sequence selected from the group consisting of (a), (b), (c), (d) and (e):
(a) Arg Met Phe Pro Asn Ala Pro Tyr Leu (SEQ ID NO: 1),
(b) Cys Tyr Thr Trp Asn Gin Met Asn Leu (SEQ ID NO: 19),
(c) Ala Pro Val Leu Asp Phe Ala Pro Pro Gly Ala Ser Ala Tyr Gly Ser Leu Gly (SEQ ID NO: 27),
(d) Lys Arg Tyr Phe Lys Leu Ser His Leu Gln Met His Ser Arg Lys His (SEQ ID NO: 32),
(e) an amino acid sequence selected from (a), (b), (c) and (d) in which one or two amino acids are replaced, deleted or added at the N- or C- terminal; and
wherein the intraocular angiogenic disease is at least one selected from the group consisting of wet-type age-related macular degeneration, myopic macular degeneration, angioid streaks, central serous chorioretinopathy, various types of retinal pigment epitheliopathy, choroidal atrophy, chroideremia, choroidal osteoma, diabetic retinopathy, retinopathy of prematurity, rubeotic glaucoma, and corneal neonascularization.

2. The method of claim 1, wherein the WT1 peptide has a binding ability to an HLA molecule.

3. The method of claim 1, wherein the WT1 peptide is capable of activating a killer T cell or a helper T cell.

4. The method of claim 1, wherein the pharmaceutical composition is administered by intracutaneous administration, subcutaneous administration, percutaneous administration, or transmucosal administration.

5. The method of claim 1, wherein the pharmaceutical composition is administered in combination with a drug for treatment of an angiogenic disease.

6. The method of claim 1, wherein the WT1 peptide consists of an amino acid sequence selected from the group consisting of (a), (b), (c), (d) and (e):
(a) Arg Met Phe Pro Asn Ala Pro Tyr Leu (SEQ ID NO: 1),
(b) Cys Tyr Thr Trp Asn Gin Met Asn Leu (SEQ ID NO: 19),
(c) Ala Pro Val Leu Asp Phe Ala Pro Pro Gly Ala Ser Ala Tyr Gly Ser Leu Gly (SEQ ID NO: 27), and
(d) Lys Arg Tyr Phe Lys Leu Ser His Leu Gln Met His Ser Arg Lys His (SEQ ID NO: 32).

* * * * *

UNITED STATES PATENT AND TRADEMARK OFFICE
CERTIFICATE OF CORRECTION

| | |
|---|---|
| PATENT NO. | : 11,369,656 B2 |
| APPLICATION NO. | : 16/592407 |
| DATED | : June 28, 2022 |
| INVENTOR(S) | : Haruo Sugiyama |

It is certified that error appears in the above-identified patent and that said Letters Patent is hereby corrected as shown below:

On the Title Page

Item (30), the Foreign Application Priority Data has been omitted. Item (30) should read:
-- (30) Foreign Application Priority Data
Dec. 11, 2014 (JP)..........................2014-251208 --

Signed and Sealed this
Eighth Day of November, 2022

Katherine Kelly Vidal
*Director of the United States Patent and Trademark Office*